United States Patent [19]

Garwood et al.

[11] Patent Number: 4,740,645
[45] Date of Patent: * Apr. 26, 1988

[54] MULTISTAGE CONVERSION OF LOWER OLEFINS WITH INTERREACTOR QUENCHING

[75] Inventors: William E. Garwood, Haddonfield; Frederick J. Krambeck, Cherry Hill, both of N.J.; John D. Kushnerick, Media, Pa.; Samuel A. Tabak, Wenonah, N.J.

[73] Assignee: Mobil Oil Corporation, New York, N.Y.

[*] Notice: The portion of the term of this patent subsequent to Jan. 5, 2005 has been disclaimed.

[21] Appl. No.: 903,915

[22] Filed: Sep. 5, 1986

Related U.S. Application Data

[63] Continuation-in-part of Ser. No. 775,906, Sep. 13, 1985, abandoned, which is a continuation-in-part of Ser. No. 650,594, Sep. 14, 1984.

[51] Int. Cl.$^4$ .......................... C07C 5/30; C07C 3/00; C07C 5/00
[52] U.S. Cl. .................... 585/329; 585/517; 585/531; 585/533; 585/255; 208/49
[58] Field of Search .............. 585/255, 329, 330, 319, 585/332, 517, 518, 531, 533; 208/46, 49

[56] References Cited

U.S. PATENT DOCUMENTS

| | | |
|---|---|---|
| 2,581,228 | 1/1952 | Bailey et al. |
| 3,827,968 | 8/1974 | Givens et al. |
| 4,150,062 | 4/1979 | Garwood . |
| 4,211,640 | 7/1980 | Garwood et al. |
| 4,433,185 | 2/1984 | Tabak . |
| 4,444,988 | 4/1984 | Capsuto et al. |
| 4,497,968 | 2/1985 | Wright et al. ...................... 585/304 |
| 4,511,750 | 4/1985 | Miller . |
| 4,517,396 | 5/1985 | Hoek et al. ........................... 585/415 |
| 4,542,247 | 9/1985 | Chang et al. ........................ 585/330 |
| 4,542,251 | 9/1985 | Miller ................................. 585/533 |
| 4,547,601 | 10/1985 | Holland et al. .................... 585/329 |
| 4,608,450 | 8/1986 | Miller ................................. 585/517 |

*Primary Examiner*—Helen M. S. Sneed
*Assistant Examiner*—Chung K. Pak
*Attorney, Agent, or Firm*—Alexander J. McKillop; Michael G. Gilman; L. G. Wise

[57] ABSTRACT

A continuous multi-stage catalytic process for converting ethene-rich lower olefinic feedstock to heavier liquid hydrocarbon product, comprising the steps of contacting ethene-rich feedstock at elevated temperature and moderate pressure in a primary stage reaction zone with a first catalyst comprising shape selective medium pore zeolite to convert at least a portion of the lower olefinic components to intermediate olefinic hydrocarbons;

cooling primary stage reaction effluent by introducing a stream of cold water sufficient to reduce the primary stage effluent to second stage reaction temperature; and contacting unreacted ethene and at least a portion of the intermediate olefinic hydrocarbons from the primary stage with nickel-containing shape selective medium pore zeolite oligomerization component at elevated temperature to provide a heavier hydrocarbon effluent stream comprising gasoline and/or distillate range hydrocarbons.

19 Claims, 9 Drawing Sheets

MULTISTAGE CONVERSION OF LOWER OLEFINS WITH INTERREACTOR QUENCHING

RELATION TO COPENDING APPLICATION

This application is a continuation-in-part of copending U.S. patent application Ser. No. 775,906, filed Sept. 13, 1985, now abandoned, which is a continuation-in-part of U.S. patent application Ser. No. 650,594 filed Sept. 14, 1984; incorporated herein by reference.

BACKGROUND OF THE INVENTION

The present invention relates to a novel technique for upgrading lower olefins, including ethene and other $C_2$–$C_8$ aliphatic hydrocarbons, to liquid products by catalytic reaction over a shape selective medium pore acid zeolite at elevated temperature. In particular, it relates to methods and apparatus for converting an ethene-rich feedstock in a multi-stage reactor system.

Recent developments in zeolite catalysts and hydrocarbon conversion processes have created interest in utilizing olefinic feedstock, for producing $C_5$+ gasoline, diesel fuel, etc. In addition to the basic work derived from ZSM-5 type zeolite catalysts, a number of discoveries have contributed to the development of new industrial process. This process has significance as a safe, environmentally acceptable technique for utilizing feedstocks that contain lower olefins, especially $C_2$–$C_5$ alkenes. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood, et al. have also contributed improved processing techniques, as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5$+ aliphatic and aromatic hydrocarbons. Operating details for typical oligomerization units are disclosed in U.S. Pat. Nos. 4,456,779; 4,497,968 (Owen, et al.) and No. 4,433,185 (Tabak), incorporated herein by reference.

In the process for catalytic conversion of olefins to heavier hydrocarbons by catalytic oligomerization using an acid crystalline zeolite, such as ZSM-5 type catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2$–$C_6$ alkenes may be converted selectively; however, the low severity distillate mode conditions do not convert a major fraction of ethene. While propene, butene-1 and others may be converted to the extent of 50% to 95% in the distillate mode, only about 10% to 30% of the ethylene component will be converted. It is an object of the present invention to provide a new technique for upgrading ethene-rich feedstocks to liquid hydrocarbons employing an efficient multi-stage system wherein at least one reactor zone includes a metallic ethene oligomerization catalyst component.

SUMMARY OF THE INVENTION

It has been found that ethene can be oligomerized by contacting an ethene-rich feedstock with a bifunctional metallic zeolite in the presence of a reducing component, such as hydrogen, by cofeeding an amount of water or water precursor effective to maintain activity of the metallic oligomerization component. Advantageously, the ethene component is converted over a Ni-ZSM-5 type catalyst in a secondary stage reactor following primary conversion of $C_3$+ olefins over HZSM-5. Adiabatic heating of the feedstock requires interstage cooling, which is achieved by injection of a cool aqueous stream into the primary stage effluent in sufficient amount to cool the cascaded olefinic stream to the desired reaction temperature for the secondary stage conversion of ethene. Accordingly, it is an object of the present invention to convert a gas stream containing ethene in the presence of hydrogen or other reducing gas to produce liquid hydrocarbons, employing a continuous multi-stage catalytic technique. Methods and apparatus are provided for contacting ethene-rich feedstock at elevated temperature and moderate pressure in a primary stage reaction zone with a first shape selective medium pore zeolite catalyst to convert a portion of the lower olefinic components to intermediate olefinic hydrocarbons. By contacting the primary stage effluent comprising unreacted ethene, reducing gas and intermediate olefins with shape selective medium pore zeolite oligomerization catalyst, such as acid Ni-ZSM-5, in a secondary stage catalytic reactor system at elevated temperature and high pressure, a heavier hydrocarbon effluent stream is produced comprising $C_{10}$–$C_{20}$ distillate range hydrocarbons. It has been found that the nickel-containing second stage catalyst may be maintained in active form which is the ionic state, even in the presence of a reducing gas, and the primary stage effluent temperature may be decreased by introducing quench water into the cascaded stream between stages.

DESCRIPTION OF PREFERRED EMBODIMENTS

Figure 1:
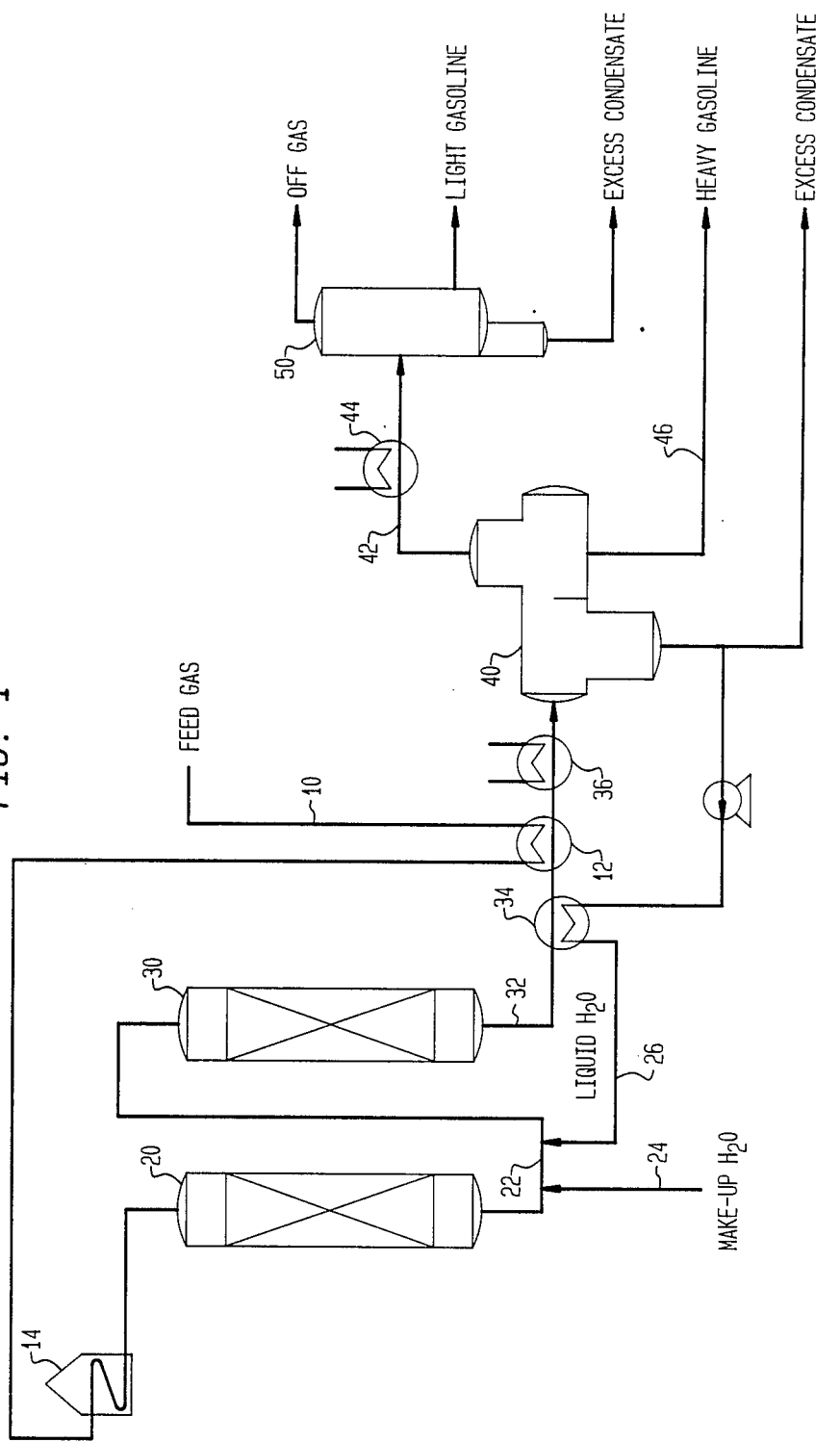
FIG. 1 is a schematic diagram depicting a two-stage process according to the present invention.

Catalyst versatility permits medium pore zeolites to be used in both the primary stage and distillate mode secondary oligomerization stage. While it is within the inventive concept to employ substantially different catalysts in these stages, it is advantageous to employ a standard ZSM-5 having a silica alumina molar ratio of 70:1, with appropriate ion exhange, impregnation or admixture to achieve the desired metallic content.

The secondary stage catalyst includes two catalytic components: (1) a metallic oligomerization component, such as Ni, and (2) a shape-selective oligomerization catalyst, such as ZSM-5 zeolite. These components may be present in admixture or combined in a unitary bifunctional solid particle. In a preferred embodiment a metal ion-exchanged zeolite, such as Ni-ZSM-5 is employed; however, it is possible to use metal-impregnated supported catalyst with metal oxide or ionically associated components. It is preferred to utilize an ethene dimerization metal or oligomerization agent effective to convert at least 50% of feedstock ethene in a continuous reaction zone under moderate process conditions. Ethene conversion metallic catalysts are disclosed in U.S. Pat. Nos. 2,581,228, 4,511,750 and European Patent Application No. 0133052.

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is characterized by strong lines as described in U.S. Pat. No. 3,702,866 (Argauer, et al.), incorporated by reference.

The oligomerization catalysts preferred for use herein include the medium pore (i.e. about 5-7 A) shape selective crystalline aluminosilicate zeolites having a silica-to-alumina ratio of at least 12, a constraint index of about 1 to 12 and acid cracking activity of about 25-250. Representative of the ZSM-5 type zeolites are ZSM-5, ZSM-11, ZSM-12, ZSM-22, ZSM-23, ZSM-35 and ZSM-38. ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245 and 4,046,839; 4,414,423; 4,417,086 and 4,517,396. The disclosures of these patents are incorporated herein by reference. A suitable catalyst for each fixed bed operation consists essentially of ZSM-5 zeolite with 35 wt.% alumina binder in the form of cyclindrical extrudates of about 1-5 mm diameter. These zeolites may be employed in their acid forms or ion exchanged with one or more suitable metal cations, such as Ni, Co and/or other metals of Periodic Groups III to VIII. Other catalysts which may be employed for converting lower olefins include the gallosilicate, borosilicate, ferrosilicate, "silicalite" and/or synthetic mordenite materials, appropriately modified for oligomerization reactions as discribed herein.

In this description, metric units and parts by weight are employed unless otherwise stated. While various reactor configurations may be used, including fluidized bed catalytic reactors, moving bed and fixed bed reactors, the invention is described for use in a plurality of fixed bed reactors operated under differing process conditions depending upon relative position in the system.

The preferred feedstock comprises at least 10 mole % ethene and may consist essentially of $C_2$-$C_6$ olefins, such normal mono-olefins and isomers thereof, and reducing gas, such as hydrogen, CO, etc. Non-deleterious components, such as paraffins, may be present.

Referring to FIG. 1, a typical process flowsheet is shown wherein the ethylene-rich $C_2^+$ olefinic feedstock is converted in a multi-stage reactor system under oligomerization conditions and moderate pressure to produce intermediate range $C_5^+$ hydrocarbons rich in gasoline range olefins. Gaseous feedstock, such as by-product light gas from cracking of petroleum fractions, is introduced through conduit 10 under process pressure, preheated in exchanger 12 and furnace 14, and contacted with oligomerization catalyst in primary reactor 20 under adiabatic conditions to convert predominantly the $C_3^+$ olefin components. The primary stage effluent stream 22 is mixed with a liquid coolant quench water injected via makeup line 24 and recycle line 26. The quench water, for example, can be injected at a rate of at least about 0.1 mole of water per mole of hydrogen. Preferably the quench water can be injected at a rate of about 0.3 to 2 moles of water per mole of hydrogen. The cooled intermediate stream, rich in ethene and intermediate olefinic hydrocarbons is passed at the desired temperature to the secondary stage reactor 30, where the cascaded stream is contacted with a metallic oligomerization catalyst or mixture, such as Ni-ZSM-5, to convert at least a significant portion of the ethene. The secondary stage effluent stream 32 is then cooled by heat exchangers 34, 12, 36 to condense an aqueous phase and heavy gasoline range liquid hydrocarbons, rich in $C_9^+$ olefins and aromatics. Phase separation unit 40 may be operated advantageously by adjusting pressure and temperature to fractionate the hydrocarbons into a light gasoline containing vapor stream 42, which is cooled by exchanger 44 prior to additional fractionation in distilation tower 50 to recover a $C_5$-$C_8$ light gasoline product, $C_1$-$C_4$ offgas containing hydrogen, etc. A heavy gasoline stream 46, rich in $C_9^+$ hydrocarbons may be blended as fuel stock or further refined in a known manner. The aqueous liquid stream, consisting essentially of water and dissolved oxygenates, is recycled under control of pump 48, exhanger 34 and conduit 26 to the primary stage. Excess condensate may be withdrawn or makeup water added, as required to meet the thermodynamic requirements or catalyst activation needs of the system.

In the system described above, a typical FCC offgas can be converted in the primary reactor starting at about 205° C. (400° F.) at the start of fresh catalyst cycle, with adiabatic heat of reaction resulting in a temperature rise of about 75° C. (135° F.) across the primary conversion zone. Injected water at a rate of about 8 parts by weight per part of hydrocarbon reduces the interstage effluent stream to about 230° C. (450° F.) for the secondary reactor, wherein the high exothermic heat generated by ethene conversion results in a temperature rise of about 135° C. (240° F.) to a final stream temperature of about 365° C. (690° F.). Other reaction conditions are given in the following description.

Stage I—Primary Oligomerization Reactor Operation

The initial olefin upgrading stage provides catalytic oligomerization reactor means containing medium pore shape selective zeolite oligomerization catalyst for converting a major amount of the $C_3^+$ olefinic hydrocarbons in the feedstock to liquid hydrocarbons comprising $C_5^+$. Product may be recovered by a fractionation system as described in U.S. Pat. Nos. 4,456,779 and 4,504,693 (Owen, et al.).

It is within the inventive concept to cascade the entire primary stage effluent stream including unreacted ethene, propene, butenes and amount of $C_5^+$ hydrocarbons from the primary stage into the secondary stage reactor, along with injected quench water. This will optimize the process and will maximize liquid production by polymerizing the lower boiling range components. However, interstage separators may be employed for between stages to effect preliminary product separation and/or provide recycle. The new process will have both a lower capital investment and operating cost than that for prior systems.

Stage II—Ethene Reactor Operation

In the secondary stage depicted in FIG. 1, the combination of catalyst and process conditions should be effective to convert a major amount (more than 50%) of ethene. This degree of reactivity may be achieved by elevated temperature, catalyst activity and space velocity to achieve the required degree of reaction severity. Ethene or other unreacted gaseous components may be present in the interstage cascade stream with hydrogen, carbon oxides, methane, nitrogen or other inert gases. A typical high severity multi-zone reactor system employs inter-zone quench, whereby the reaction exotherm can be carefully controlled to prevent excessive temperature above the normal moderate range of about 100° to 450° C., preferably 250° C. to 400° C. Advantageously, the space velocity (LHSV based on olefin feed) is about 0.5 to 1. Heat exchangers provide cooling and reduce the effluent to fractionation temperature. Heat exchangers may recover heat from the effluent stream prior to fractionation. It is preferred to operate the reactors at moderate pressure of about 200 to 2900 kPa (15–400 psig).

The reactor system may contain multiple downflow adiabatic catalytic zones in a single reactor vessel. The weight hourly space velocity (WHSV, based on total fresh feedstock) is about 0.1–2 LHSV. In this system recycle ratio of light gas is not necessary, and the cost of recompressing a recycled diluent is avoided.

Figure 2:
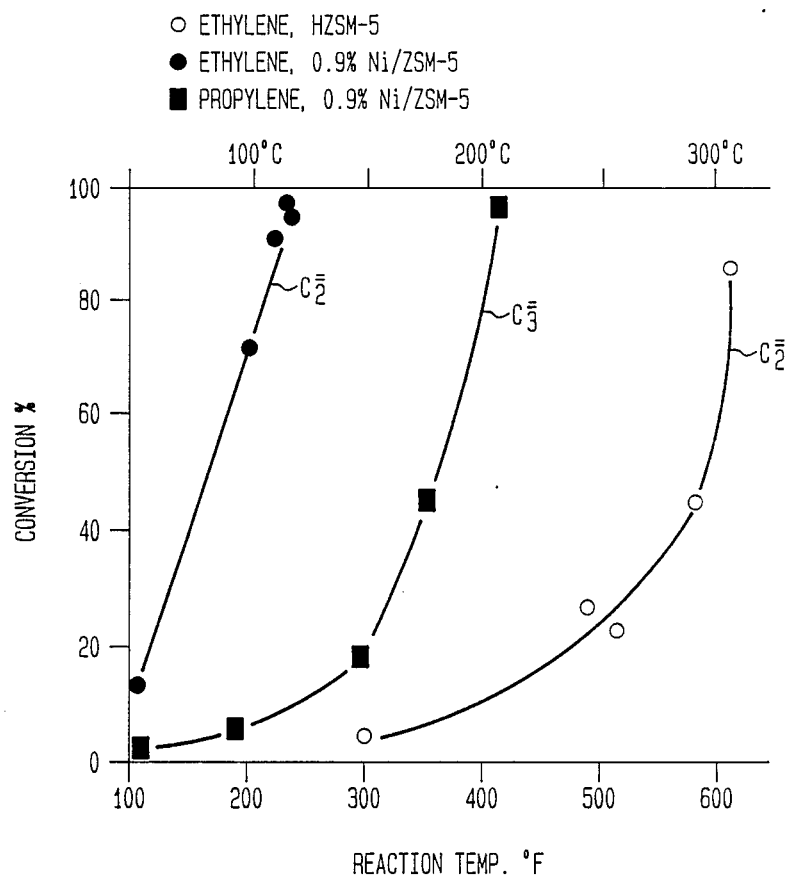
FIG. 2 is a graphic plot of $C_2$–$C_3$ conversion vs reaction temperature.

In order to demonstrate the improvement in ethene conversion using a bifunctional catalyst, a series of comparative runs are conducted in a fixed bed tubular reactor. The unexchanged HZSM-5 catalyst is a standard aluminosilicate zeolite having an acid value of about 180, a silica-to-alumina ratio of 70:1 and crystalline size of about 0.02 to 0.05 microns. The catalyst is prepared as an extrudate having a particle size of 14 to 25 mesh size (U.S.G.) with 35 wt % alumina binder. The calcined acid form of HZSM-5 is at least partially ion-exchanged with nickel and recalcined to produce a bifunctional catalyst containing 0.9 wt % Ni. The conversion plot in FIG. 2 is obtained under substantially isothermal conditions at 2900 kPa (400 psig) under steady state continuous conditions at an average space velocity (WHSV) of about 0.5 parts by weight of alkene feed per part of catalyst per hour.

The conversion of ethene ($C_2=$) using HZSM-5 catalyst requires excessively high temperature, above 280° C., to obtain more than 50% conversion, thus increasing aromatics yield in the primary stage. By contrast, the acidic Ni-ZSM-5 bifunctional catalyst converts a major amount of ethene at 100° C. or below. The comparative runs for propylene ($C_3=$) feed shows no significant improvement using the bifunctional catalyst.

The conversion of ethene over the Ni-treated ZSM-5 catalyst is further investigated at moderate pressure from about 600 to 2900 kPa and temperatures of about 40° to 315° C. (100° to 600° F.) using the above described catalyst. The initial run is conducted with fresh calcined catalyst, purged in situ at about 480° C. with $N_2$. Table 1 shows the lower pressure runs (1L–14L) and Table 2 the higher pressure runs (1H–14H).

TABLE 1

600 kPa (75 psig)
Ethylene, 0.9 wt % Ni/ZSM-5
0.5–0.6 WHSV, 100–600° F.

| | Run No., | | | | | | | | | | | | | |
|---|---|---|---|---|---|---|---|---|---|---|---|---|---|---|
| | -1L | -2L | -3L | -4L | -5L | -6L | -7L | -8L | -9L | -10L | -11L | -12L | -13L | -14L |
| $C_2=$, WHSV | 0.5 | 0.5 | 0.5 | 0.5 | 0.5 | 0.5 | 0.5 | 0.5 | 0.5 | 0.5 | 0.6 | 0.6 | 0.6 | 0.5 |
| Av. Cat. Temp, °F. | 102 | 151 | 199 | 252 | 303 | 350 | 397 | 446 | 450 | 500 | 500 | 548 | 549 | 598 |
| Mat. Bal., Time, Hrs | 16½ | 1 | 17½ | 1 | 1 | 16½ | 21 | 96 | 24 | 21½ | 21 | 21½ | 21½ | 21½ |
| Days on stream | 0.7 | 0.8 | 1.5 | 1.5 | 1.5 | 2.2 | 3.1 | 7.1 | 8.1 | 9.0 | 9.9 | 10.8 | 11.7 | 12.6 |
| $C_2=$ Conv., wt % | 6 | 6 | 7 | 9 | * | 27 | 29 | 20 | 13 | 59 | 21 | 45 | 38 | 60 |
| Yields, Wt % (NLB) | | | | | | | | | | | | | | |
| $C_1$ | — | — | — | — | — | — | — | — | — | — | — | — | — | 0.1 |
| $C_2$'s Total | 94.2 | 94.3 | 93.1 | 91.5 | | 73.3 | 70.7 | 80.4 | 87.1 | 40.8 | 79.1 | 55.2 | 62.3 | 41.3 |
| $C_2=$ | 94.2 | 94.2 | 93.1 | 91.5 | | 73.3 | 70.7 | 80.4 | 87.1 | 40.8 | 78.9 | 54.6 | 62.0 | 39.7 |
| $C_2$ | — | — | — | — | — | — | — | — | — | — | 0.2 | 0.6 | 0.3 | 1.6 |
| $C_3$'s Total | 2.8 | 2.6 | 2.5 | 2.8 | — | 2.6 | 2.7 | 2.2 | 2.9 | 7.7 | 2.6 | 2.3 | 2.9 | 2.3 |
| $C_3=$ | 0.2 | 0.4 | — | 0.4 | — | 0.7 | 0.6 | — | 0.5 | 6.3 | 0.2 | 0.7 | 1.1 | 1.0 |
| $C_3$ | 2.6 | 2.4 | 2.5 | 2.4 | — | 1.9 | 2.1 | 2.2 | 2.4 | 1.4 | 2.4 | 1.6 | 1.8 | 1.3 |
| $C_4$'s Total | 2.1 | 2.5 | 3.1 | 5.3 | — | 19.3 | 18.7 | 10.5 | 2.0 | 23.2 | 3.4 | 8.7 | 8.0 | 13.6 |
| $C_4=$ | 2.0 | 2.5 | 3.1 | 5.3 | — | 19.3 | 18.5 | 10.2 | 1.9 | 22.3 | 3.0 | 7.2 | 7.0 | 11.1 |
| $iC_4$ | — | — | — | — | — | — | 0.1 | — | — | 0.9 | 0.2 | 1.2 | 0.8 | 2.5 |
| $nC_4$ | 0.1 | — | — | — | — | — | 0.1 | 0.3 | 0.1 | — | 0.2 | 0.3 | 0.2 | 0.6 |
| $C_5$'s Total | 0.2 | 0.4 | 0.4 | 0.4 | — | 0.7 | 1.0 | 1.4 | 1.4 | 12.1 | 2.8 | 7.5 | 6.3 | 1.1 |
| $C_5=$ | 0.1 | 0.4 | 0.1 | 0.4 | — | 0.7 | 0.9 | 1.4 | 0.8 | 8.8 | 2.5 | 6.3 | 5.7 | 0.0 |
| $i$-$C_5$ | 0.1 | — | 0.3 | — | — | — | 0.1 | — | 0.6 | 3.3 | 0.3 | 1.1 | 0.6 | 1.7 |
| $n$-$C_5$ | — | — | — | — | — | — | — | — | — | — | — | 0.1 | — | 0.4 |
| $C_6$–330° F. | | — | | — | — | 4.0 | 5.0 | 1.7 | 4.4 | 10.9 | 9.0 | 17.6 | 20.5 | 20.2 |
| 330–650° F. | 0.7 | — | 0.9 | — | — | 1 | 1.9 | 3.8 | 2.2 | 5.3 | 3.1 | 8.7 | 3.1 | 10.9 |
| 650° F.+ | — | — | — | — | — | 0.1 | 0.1 | 0.4 | 0.1 | 0.1 | 0.1 | 0.1 | 0.1 | 0.1 |

*No material balance available.
Tubular reactor or fluid bed to remove exotherm.

TABLE 2

2900 kPa (400 psig)
Ethylene, 0.9 wt % Ni/ZSM-5B
0.4–0.6 WHSV, 100–500° F.

| | Run No., | | | | | | | | | | | | | |
|---|---|---|---|---|---|---|---|---|---|---|---|---|---|---|
| | -1H | -2H | -3H | -4H | -5H | -6H | -7H | -8H | -9H | -10H | -11H | -12H | -13H | -14H |
| $C_2=$, WHSV | 0.6 | 0.5 | 0.5 | 0.5 | 0.5 | — | 0.5 | 0.6 | 0.5 | 0.4 | 0.4 | 0.4 | 0.4 | 0.4 |
| Av. Cat. Temp, °F. | 108 | 216 | 254 | 250 | 242 | 265 | 262 | 258 | 289 | 298 | 351 | 402 | 447 | 493 |
| Mat. Bal., Time, Hrs | 2 | 16 | 18 | 19 | 21½ | — | 16½ | 20½ | 21½ | 21 | 21 | 21 | 21 | 21 |
| Days on stream | 0.1 | 0.8 | 1.5 | 2.3 | 3.2 | 4.0 | 4.7 | 5.6 | 6.4 | 7.3 | 8.2 | 9.0 | 9.9 | 10.8 |
| $C_2=$ Conv., wt % | 14 | 70 | 95 | 97 | 92 | * | 94 | 54 | 62 | 63 | 63 | 62 | 52 | 60 |
| Yields, Wt % (NLB) | | | | | | | | | | | | | | |
| $C_1$ | — | — | — | — | — | * | — | — | — | — | — | — | — | — |
| $C_2$'s Total | 85.8 | 30.4 | 4.8 | 3.2 | 8.6 | * | 6.1 | 46.4 | 37.6 | 37.6 | 37.0 | 38.2 | 49.1 | 40.6 |
| $C_2=$ | 85.8 | 30.4 | 4.8 | 2.7 | 8.4 | * | 6.0 | 46.4 | 37.6 | 37.5 | 36.8 | 37.9 | 48.2 | 39.5 |
| $C_2$ | — | — | — | 0.5 | 0.2 | * | 0.1 | — | — | 0.1 | 0.2 | 0.3 | 0.9 | 1.1 |
| $C_3$'s Total | 3.9 | 3.1 | 2.1 | 2.5 | 3.8 | * | 2.8 | 2.9 | 2.8 | 3.4 | 2.7 | 1.9 | 1.7 | 1.6 |
| $C_3=$ | 1.2 | 2.1 | 1.9 | 2.3 | 3.6 | * | 2.6 | 1.7 | 1.8 | 2.4 | 1.7 | 0.7 | 0.2 | 0.3 |
| $C_3$ | 2.7 | 1.0 | 0.2 | 0.2 | 0.2 | * | 0.2 | 1.2 | 1.0 | 1.0 | 1.0 | 1.2 | 1.5 | 1.3 |
| $C_4$'s Total | 9.0 | 49.8 | 40.8 | 42.7 | 50.6 | * | 37.4 | 35.6 | 35.8 | 37.2 | 36.6 | 28.0 | 14.6 | 5.4 |
| $C_4=$ | 9.0 | 49.8 | 40.8 | 42.7 | 50.5 | * | 37.3 | 35.4 | 35.5 | 37.1 | 36.4 | 27.7 | 13.9 | 3.73 |
| $iC_4$ | — | — | — | — | 0.1 | * | 0.1 | 0.1 | — | — | 0.1 | 0.2 | 0.4 | 1.31 |
| $nC_4$ | — | — | — | — | — | * | — | 0.1 | 0.3 | 0.1 | 0.1 | 0.1 | 0.3 | 0.4 |
| $C_5$'s Total | 0.5 | 2.2 | 2.2 | 2.5 | 3.4 | * | 2.6 | 1.7 | 2.5 | 2.3 | 2.1 | 2.8 | 3.4 | 2.7 |
| $C_5=$ | 0.5 | 2.1 | 2.1 | 2.3 | 3.4 | * | 2.6 | 1.6 | 2.3 | 2.3 | 2.0 | 2.6 | 3.1 | 1.5 |
| $i$-$C_5$ | — | 0.1 | 0.1 | 0.2 | — | * | — | 0.1 | 0.2 | — | 0.1 | 0.2 | 0.3 | 1.1 |
| $n$-$C_5$ | — | — | — | — | — | * | — | — | — | — | — | — | — | 0.1 |
| $C_6$-330° F. | — | 7.8 | 34.6 | 35.8 | 25.2 | * | 36.8 | 12.5 | 11.7 | 13.8 | 14.0 | 15.1 | 13.1 | 10.9 |
| 330–650° F. | 0.8 | 6.2 | 14.0 | 11.3 | 7.4 | * | 12.3 | 0.9 | 7.9 | 4.9 | 6.3 | 11.4 | 15.0 | 25.8 |
| 650° F.+ | — | 0.4 | 1.5 | 2.0 | 1.0 | * | 2.0 | 0.1 | 1.7 | 0.8 | 1.3 | 2.6 | 3.1 | 6.0 |

*Reactor plugged.

Figure 3:
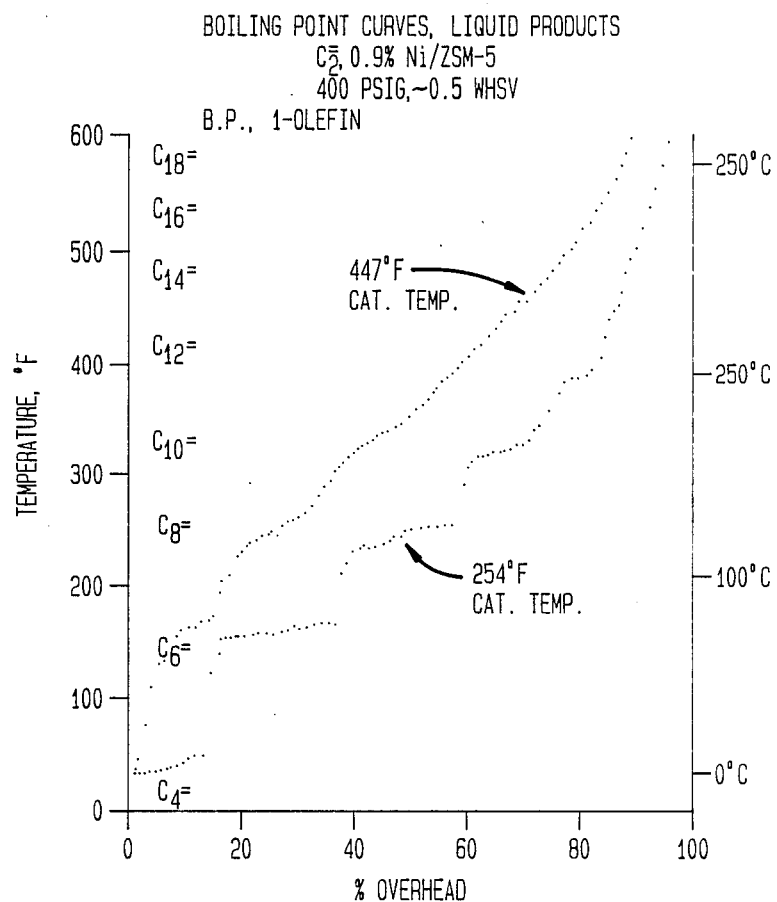
FIG. 3 is a distillation curve for hydrocarbon products.

Liquid product from two different runs at 2900 kPa are plotted as a distillation curve in FIG. 3, using a standard boiling point test (D-2887). Runs 3 and 13 compare significantly aged and fresher catalyst at two different reaction temperatures.

Figure 4:
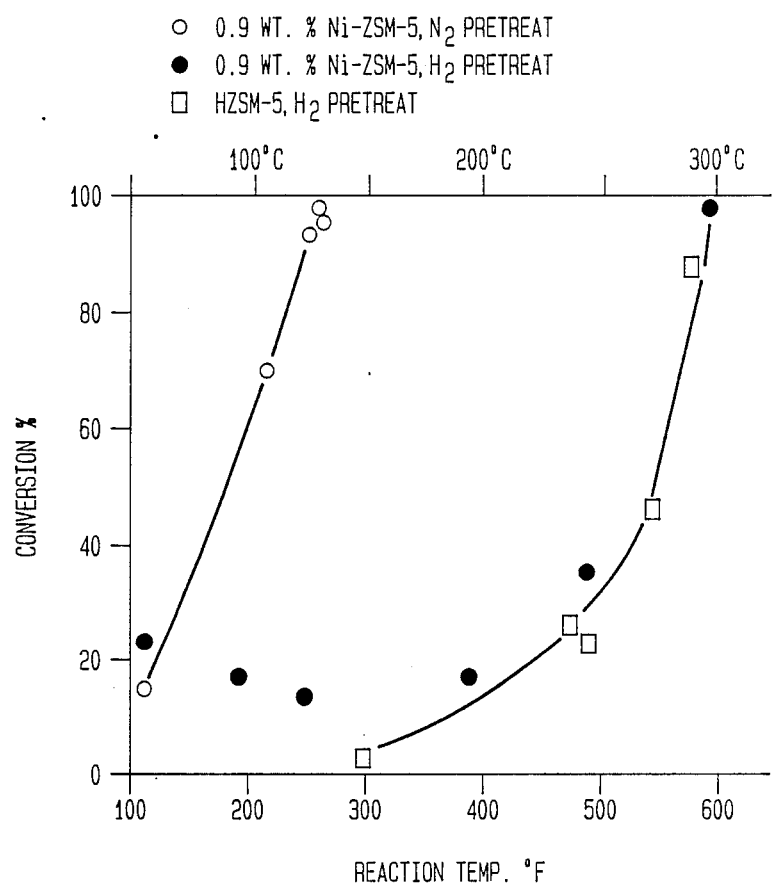
FIG. 4 is a graphic plot of ethene conversion using different catalysts.

In order to demonstrate how the preferred nickel treated ZSM-5 catalyst is affected by metal valence state, comparative runs are made in which the nickel ion exchanged ZSM-5 is treated in a reducing atmosphere. The graphic plot in FIG. 4 compares conversion of ethylene over HZSM-5, 0.9% Ni-ZSM-5 (ionically exchanged, as in FIG. 2) and reduced nickel catalyst. The reduced nickel is produced by calcining the exchanged Ni-ZSM-5 at 480° C. in hydrogen instead of nitrogen, thus providing a material in which the major amount of nickel is present in the reduced metallic state. While the reduced catalyst has significant activity initially, it decreases rapidly as temperature is increased during the run, approaching the lower activity of HZSM-5.

Figure 5:
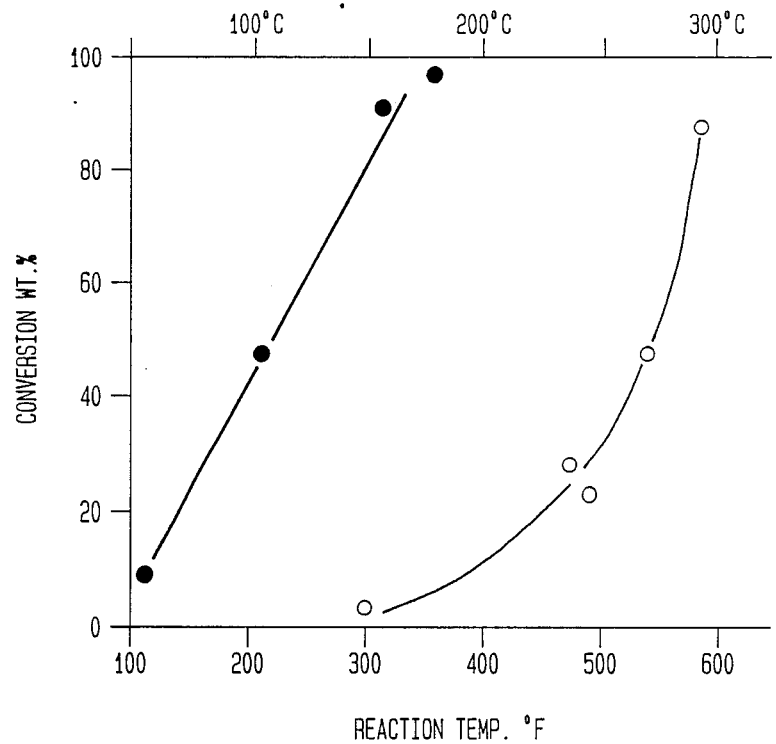
FIG. 5 is a plot of $C_2$–$C_3$ conversion using acid catalyst without metal treatment.

The runs depicted in FIG. 5 show ethylene and propylene conversions over HZSM-5 (acid value=180) from ambient temperatures to complete conversion under comparable process conditions. In the absence of the metal oligomerization component, conversion of ethylene is observed to be considerably less than propylene.

EXAMPLES 15–17

Continuous runs are made in a tubular reactor unit employing standard ZSM-5 (65%) extrudate catalyst at elevated pressure. Example 15 employs HZSM-5 having an acid cracking activity (alpha value) of about 200. Examples 16 and 17 employ nickel-exchanged (0.9 wt.%) acid ZSM-5. The fresh feedstock for Examples 15 and 17 contain 12.6 mol % ethene ($C_2=$), 7.9% propene ($C_3=$), 53.6% $N_2$ and 25.9% $H_2$. In Example 16 the propene is replaced with with nitrogen, giving a total of 61.5% $N_2$. In Example 15 no water is injected with the feed. In Example 16 and 17 about 0.3 moles of water per mole of hydrogen is injected at the reactor inlet. Examples 15–17 are conducted at similar conversion rates and show the yields for each run. The results of these runs are set forth in Table 3.

TABLE 3

| Example | 15 | 16 | 17 |
|---|---|---|---|
| Days on stream | 7.5 | 7.3 | 15.5 |
| OPERATING CONDITIONS | | | |
| WHSV on HC feed, 1/hr. | 1.00 | 0.98 | 0.56 |
| Reactor Pressure, KPA | 1825 | 1825 | 3204 |
| Gas recycle ratio, MOL/MOL | 2.0 | 2.0 | 2.0 |
| Avg reactor temp., °C. | 376 | 261 | 286 |
| Reactor 1 inlet, °C. | 321 | 176 | 215 |
| T, °C. | 75 | 183 | 147 |
| $C_2=$ PP at RXT inlet, KPA | 87.6 | 106.4 | 165.0 |
| $C_3=$ PP at RXT inlet, KPA | 33.6 | 49.4 | 4.1 |
| Moles water/mole $H_2$ at inlet | 0 | 0.3 | 0.3 |
| Propane/Propene Ratio (RI) | 1.13 | 1.14 | 1.20 |
| YIELDS ON HYDROCARBON, WT % | | | |
| $C_5+$ including alkylate | 82.3 | 75.4 | 72.1 |
| potential alkylate | 9.3 | 9.4 | 10.4 |
| $C_4+$ | 86.1 | 79.2 | 73.1 |
| $C_5+$ | 73.0 | 66.0 | 61.7 |
| $C_5$'s | 14.8 | 13.3 | 10.8 |
| $NC_4$ | 1.7 | 1.7 | 1.6 |
| $IC_4$ | 4.8 | 4.8 | 5.4 |
| $C_4=$ | 6.6 | 6.7 | 4.3 |
| $C_3$ | 2.8 | 2.4 | 2.3 |
| $C_3=$ | 2.5 | 2.1 | 1.9 |
| $C_2$ | 0.6 | 7.1 | 10.4 |
| $C_2=$ | 8.0 | 9.2 | 12.3 |
| $C_1$ | 0.1 | 0.0 | 0.0 |
| CONVERSION, WT % | | | |
| $C_2=$ | 83.7 | 84.0 | 88.0 |
| $C_3=$ | 94.7 | 95.2 | 0.0 |
| Total feed olefin | 89.0 | 88.9 | 88.0 |
| PRODUCT PROPERTIES | | | |
| Raw octane, R + O | 93.1 | — | 89.8 |
| Raw Octane, M + O | — | — | — |
| S.G. at 15.6° C. | 0.734 | 0.736 | 0.750 |
| D2887 B.P. DISTRIBUTION, °C. | | | |
| 5 | — | 18 | 22 |
| 10 | — | 35 | 40 |

TABLE 3-continued

| Example | 15 | 16 | 17 |
|---|---|---|---|
| 30 | — | 73 | 91 |
| 50 | — | 109 | 123 |
| 70 | — | 139 | 151 |
| 90 | — | 181 | 188 |
| 95 | — | 201 | 201 |
| 99.5 | — | 268 | 263 |

Figure 6:
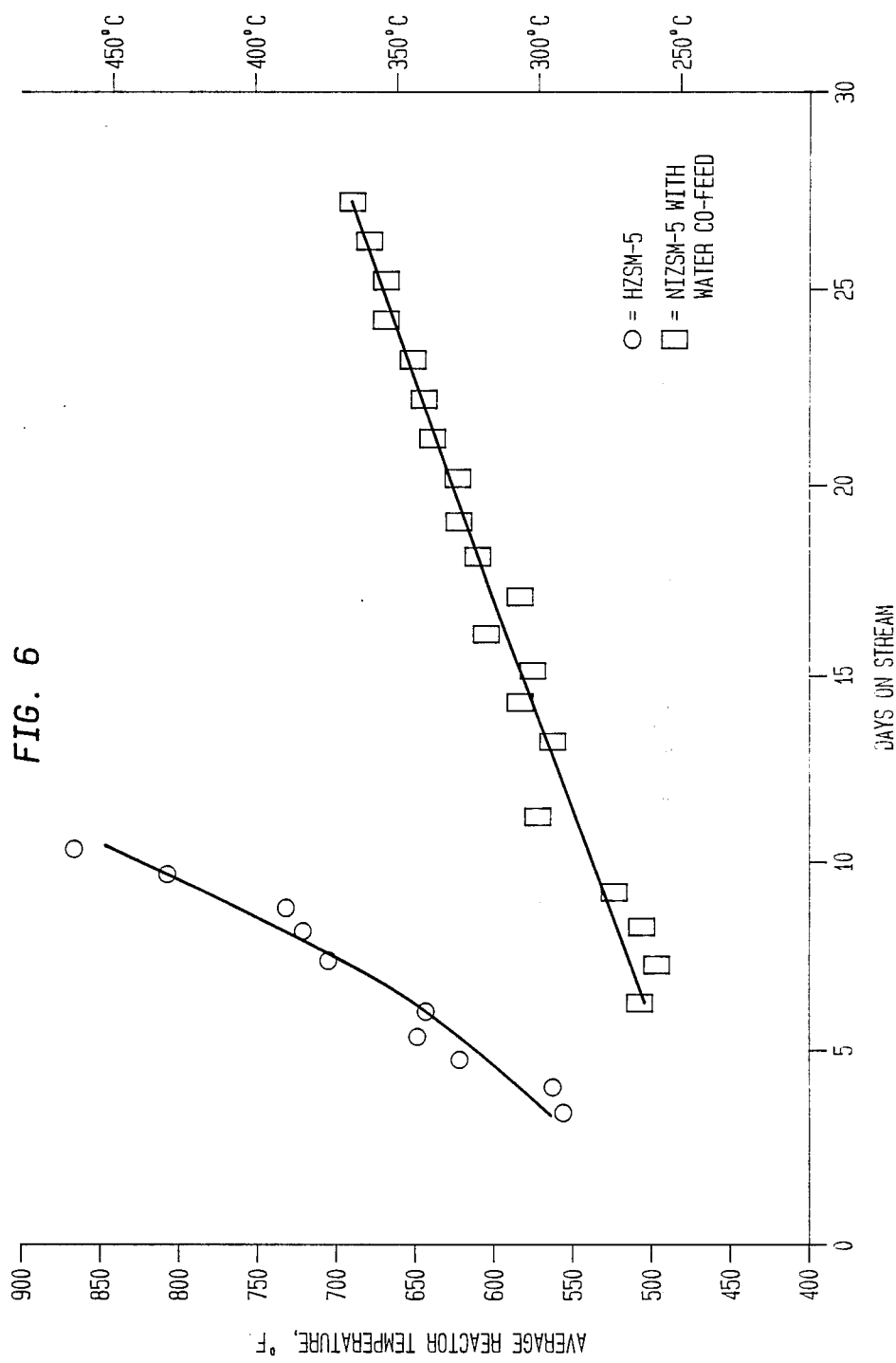
FIGS. 6 and 7 plot reactor temperature vs. time.
Figure 7:
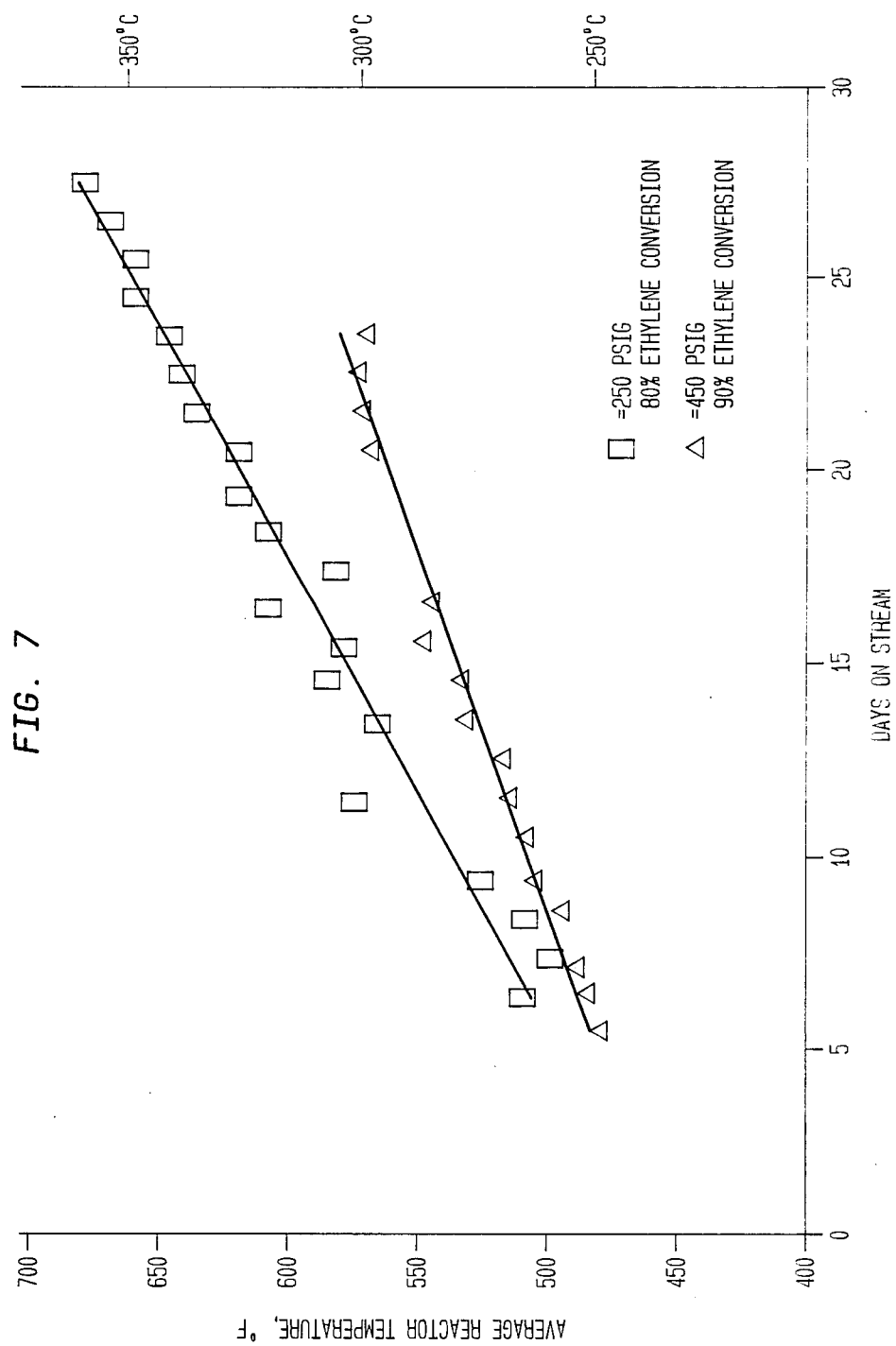

These examples are depicted graphically in FIGS. 6 and 7 for long term continuous runs. FIG. 6 shows the advantage of NiZSM-5 with water cofeed over HZSM-5. Catalyst deactivation rate is reduced by about a factor of 5. These average reactor temperatures are normalized to 80% ethylene conversion. FIG. 7 shows the advantage of operating at increased pressures. By raising total pressure from 1825 kPa (250 psig) to 3200 kPa (450 psig), it is possible to operate at 10% higher ethylene conversion and still further reduce catalyst deactivation rate by about a factor of 1.5. The average reactor temperatures for the 450 psig experiment have been normalized to a constant 90% ethylene conversion.

Figure 8:
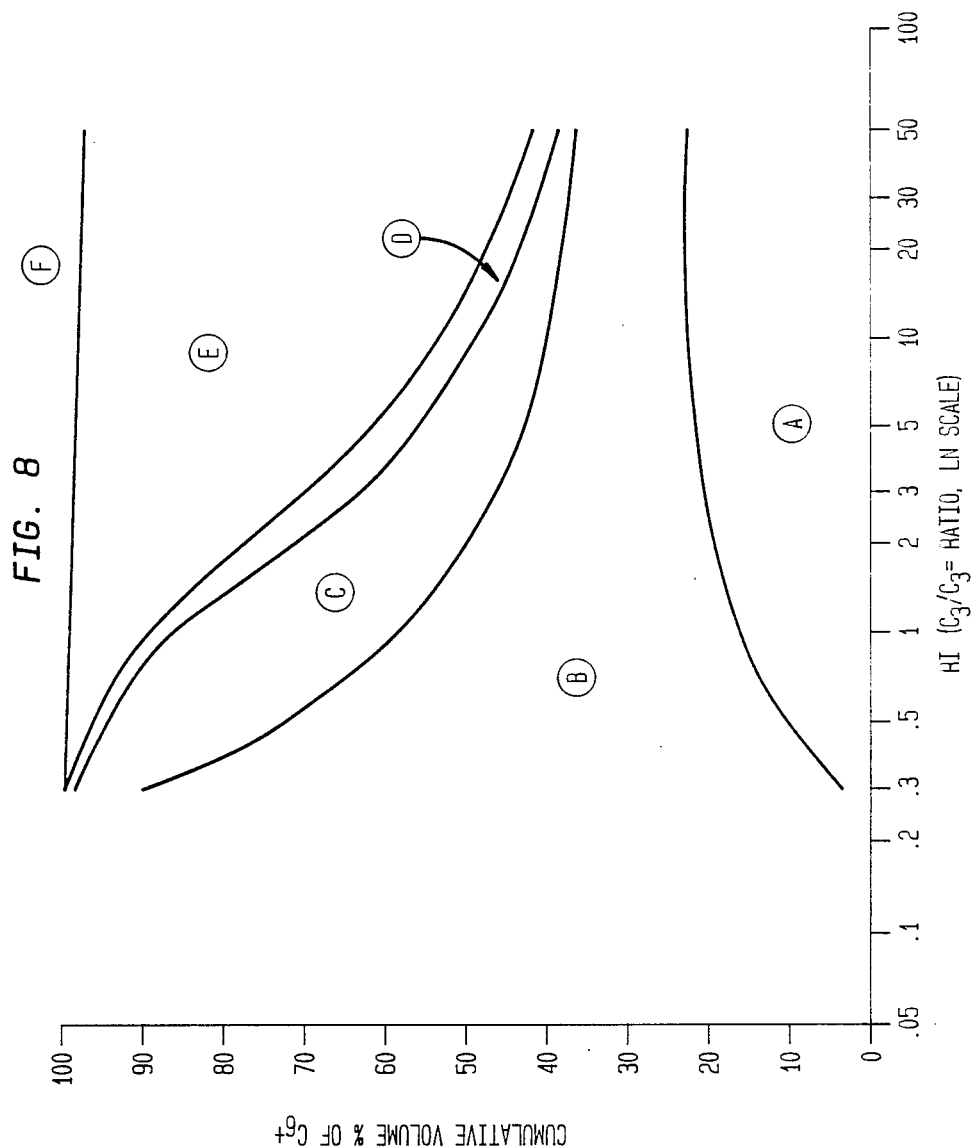
FIG. 8 plots liquid product composition vs reaction severity.

FIG. 8 is a semi-log plot depicting product distribution and shows how the composition of the $C_6^+$ gasoline product changes as processing severity increases. Severity is indicated by RI, the weight ratio of propane to propene in the unit's product. Hydrocarbon class zones are indicated by letters, which represent the following:

| Zone | Formula | Hydrocarbon Type |
|---|---|---|
| A | $C_nH_{2n+2}$ | Paraffin |
| B | $C_nH_{2n}$ | Olefin or Naphthene |
| C | $C_nH_{2n-2}$ | Cyclo-olefin di-olefin |
| D | $C_nH_{2n-4}$ | Cyclo-diolefin or Tri-olefin |
| E | $C_nH_{2n-6}$ | Aromatic |
| F | $C_nH_{2n-8}$ | Multi-cyclic |

Figure 9:
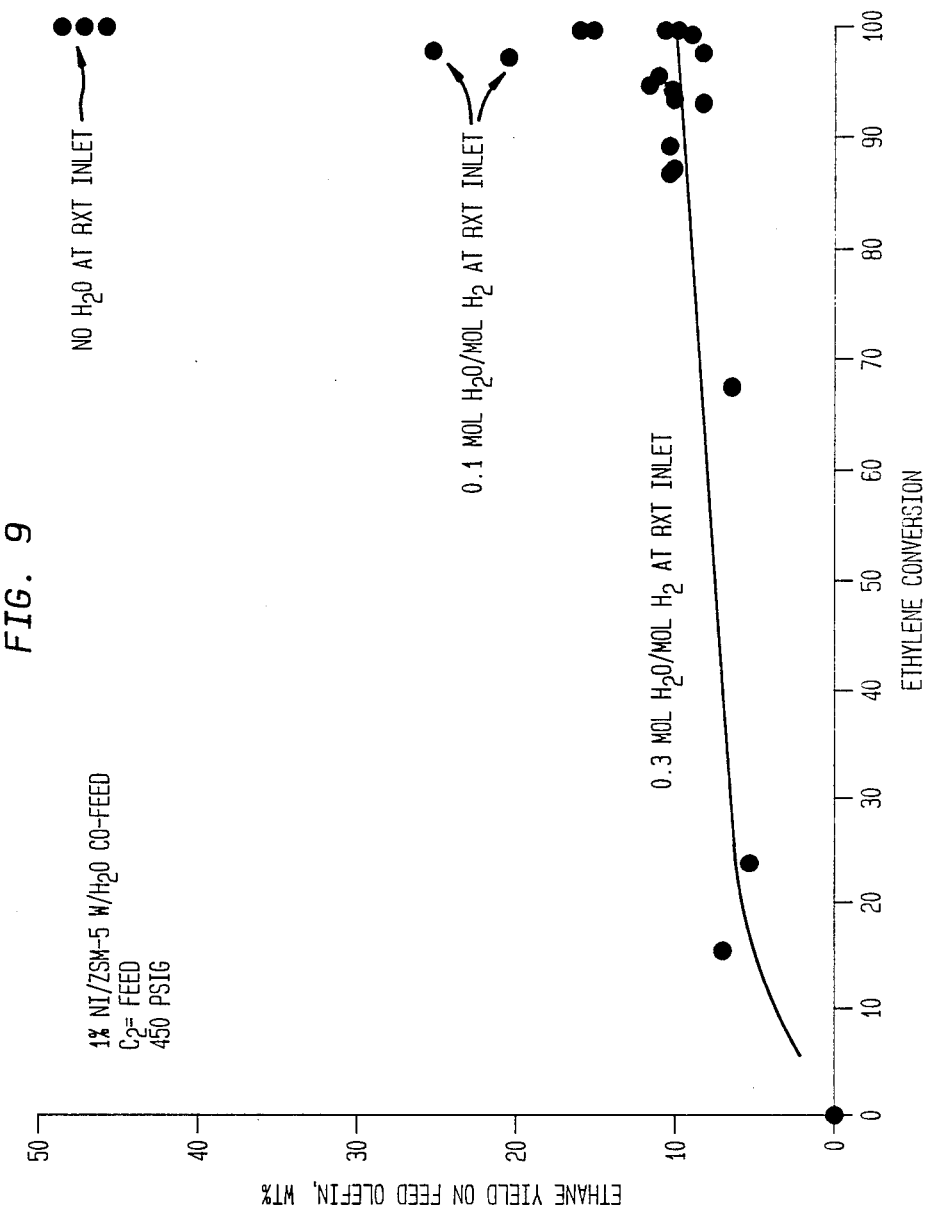
FIG. 9 shows the effects of water cofeeding.

FIG. 9 graphically depicts the effect of cofeeding water selectively in Example 17. This plot shows that with NiZSM-5, water cofeed, for example, at a rate of 0.3 mole of water per mole of hydrogen is required to maintain selectivity to higher molecular weight product. Without the water, ethylene hydrogenation becomes significant. These data are set forth in Table 4 following:

TABLE 4
Reversible Effect of Water Removal

| Example 17 | With $H_2O$ | $H_2O$ Removed | $H_2O$ Restored |
|---|---|---|---|
| Time on stream (days) | 16.5 | 17.5 | 20.5 |
| $H_2O/H_2$ mol/mol (reactor inlet) | 0.3 | 0.0 | 0.3 |
| Ethane Yield on Olefin, Wt % | 10.7 | 48.6 | 11.7 |
| $C_5+$ Yield on Olefin, Wt % | 62.7 | 16.8 | 62.9 |
| $C_2=$ Conversion | 90.1 | 99.9 | 95.5 |
| Average Reactor Temperature °C./(°F.) | 285(544) | 297(567) | 299(570) |
| RI (reaction severity index) | 1.43 | 67.75 | 2.54 |

This example shows that catalyst selectivity changes are reversible as water is removed from and returned to the reactor. The FIG. 9 also graphically depicts the effect on selectivity of cofeeding water at a rate of about 0.1 mole of water per mole of hydrogen.

EXAMPLE 18

A continuous two-stage conversion is conducted employing the system depicted in FIG. 1. The feedstock given in Table 5 is a typical FCC by-product light gas, minus trace components, such as amines and sulfides. The primary stage catalyst is standard HZSM-5 and the second stage catalyst is Ni-exhanged acid ZSM-5, as described above in Ex. 15-17.

TABLE 5
FCC Light Gas Composition Feedstock (Ex. 18)

| Component | Mol % |
|---|---|
| $N_2$ | 14.4 |
| $H_2$ | 25.9 |
| $C_1$ | 26.6 |
| $C_2$ | 10.4 |
| $C_2=$ | 12.6 |
| $C_3$ | 1.7 |
| $C_3=$ | 7.2 |
| $nC_4$ | 0.1 |
| $iC_4$ | 0.4 |
| $C_4=$ | 0.7 |
| | 100.0 |

The second stage effluent hydrocarbon calculated yields are given in Table 6, including raw liquid properties and boiling range data.

TABLE 6
Product Hydrocarbons

| Second Stage Product Yield (Wt. % of Feed Olefins) | |
|---|---|
| $C_1$ | 0.0 |
| $C_2$ | 4.4 |
| $C_2=$ | 16.4 |
| $C_3$ | 1.2 |
| $C_3=$ | 1.4 |
| $nC_4$ | 0.8 |
| $iC_4$ | 2.8 |
| $C_4=$ | 5.5 |
| $C_5=$ | 67.5 |
| Unstabilized Raw Liquid Product Properties | |
| SGr (20° C.) | 0.737 |
| R + O Octane | 92.2 |
| M + O Octane | 80.4 |
| Boiling Point Distribution (°F.) (D2887) | |
| 5 wt. % | 75 |
| 10 wt. % | 104 |
| 30 wt. % | 182 |
| 50 wt. % | 242 |
| 70 wt. % | 294 |
| 90 wt. % | 371 |
| 95 wt. % | 410 |
| EP | 533 |

While the invention has been described by specific examples and embodiments, there is no intent to limit the inventive concept except as set forth in the following claims.

We claim:

1. A continuous multi-stage catalytic process for converting ethene-rich lower olefinic feedstock containing reducing gas to heavier liquid hydrocarbon product comprising gasoline and/or distillate range hydrocarbons, comprising the steps of contacting said ethene-rich feedstock under oligomerization conditions at elevated temperature and moderate pressure in a primary stage reaction zone with a first catalyst comprising shape selective medium pore zeolite to convert at least a portion of the lower olefinic feedstock to intermediate olefinic hydrocarbons and obtain a primary stage reaction effluent comprising unreacted ethene, reducing gas and said intermediate olefinic hydrocarbons;

cooling said primary stage reaction effluent by introducing a steam of cold water sufficient to reduce the primary stage effluent to second stage reaction temperature; and contacting a portion of the cooled primary stage reaction effluent containing unreacted ethene, reducing gas and at least a portion of the intermediate olefinic hydrocarbons and said water with a secondary stage ionic nickel-containing shape selective medium pore zeolite oligomerization catalyst in a second stage reaction zone at elevated temperature to produce said heavier liquid hydrocarbon product comprising gasoline and/or distillate range hydrocarbons; said water being present in an amount sufficient to maintain selectivity of the nickel zeolite catalyst to said heavier liquid hydrocarbon product.

2. The process of claim 1 wherein the feedstock comprises at least 5 mole % ethene.

3. The process of claim 2 wherein the feedstock consists essentially of $C_2$–$C_6$ olefins and hydrogen, and wherein the secondary stage reaction zone nickel zeolite catalyst consists essentially of ionic Ni exchanged acid ZSM-5.

4. The process of claim 1 wherein said primary and secondary stage catalysts have an acid value of about 10 to 250.

5. The process of claim 1 wherein the secondary stage catalyst converts at least 50% of ethene in a continuous fixed bed process at a pressure not greater than about 2900 kPa at a temperature of about 100° to 450° C.

6. The process of claim 1 wherein the zeolite of the secondary stage catalyst consists essentially of a crystalline aluminosilicate zeolite having a silica-to-alumina molar ratio greater than 12 and a constraint index of about 1 to 12.

7. The process of claim 1 wherein said quench water is recovered from the secondary stage effluent and reused to cool said primary stage reaction effluent.

8. A continuous multi-stage catalytic process for converting ethene-rich lower olefinic feedstock containing hydrogen to heavier hydrocarbon product comprising gasoline and/or distillate range hydrocarbons, comprising the steps of contacting the ethene-rich feedstock under oligomerization conditions in a primary stage reaction zone with a first shape selective medium pore acid zeolite oligomerization catalyst to convert a portion of the lower olefinic components to form a primary stage reaction effluent comprising intermediate olefinic hydrocarbons;

quenching said primary stage effluent with liquid quench water;

cascading the resultant cooled primary stage effluent comprising unreacted ethene, hydrogen, water and at least a portion of the intermediate olefinic hydrocarbons for contact with a second catalyst comprising an ionic nickel ethene oligomerization component and a shape selective medium pore acid zeolite oligomerization component in a secondary stage catalytic reaction zone at elevated temperature and pressure to obtain said heavier hydrocarbon product comprising gasoline and/or distillate range hydrocarbons; said water being present in an amount sufficient to maintain selectivity of said second catalyst to said heavier hydrocarbon product.

9. The process of claim 8 further comprising the steps of cooling said heavy hydrocarbon product to condense at least a portion of the intermediate hydrocarbons, separating the cooled heavy hydrocarbon product in a phase separation zone into a light gas stream and a condensed liquid hydrocarbon stream.

10. The process of claim 8 wherein the feedstock comprises at least 5 mole % ethene.

11. The process of claim 8 wherein the second catalyst consists essentially of Ni-exchanged ZSM-5 zeolite.

12. The process of claim 8 wherein the feedstock is converted in the absence of added diluent or recycled hydrocarbons.

13. The process of claim 8 wherein the oligomerization conditions in the primary stage reaction zone comprise adiabatic conversion conditions maintained to convert $C_3^+$ olefins in an amount to control exothermic temperature rise not more than 75° C. above inlet temperature.

14. The process of claim 8 wherein the liquid quench water is injected at a rate of at least about 0.1 moles of water per mole of hydrogen.

15. The process of claim 8 wherein the liquid quench water is injected at a rate of about 0.3 to 2 moles of water per mole of hydrogen.

16. A continuous multi-stage catalytic process for converting lower olefinic feedstock mixture containing ethene, $C_3^+$ olefin and hydrogen to liquid hydrocarbon product comprising gasoline and/or distillate range hydrocarbons, comprising the steps of contacting said feedstock under oligomerization conditions at elevated temperature and moderate pressure in a primary stage reaction zone with a first oligomerization zeolite catalyst to convert at least a portion of $C_3^+$ olefin to intermediate olefinic hydrocarbons;

recovering the resultant primary stage effluent stream containing unreacted ethene, hydrogen and intermediate olefinic hydrocarbons;

cooling said primary stage reaction effluent by introducing a stream of cold quench water sufficient to reduce the primary stage effluent temperature; and contacting at least a portion of the cooled primary stage effluent comprising the unreacted ethene, hydrogen, intermediate olefinic hydrocarbons and said water in a secondary stage reaction zone with a second oligomerization catalyst comprising ionic nickel-containing shape selective medium pore zeolite at elevated temperature to produce said liquid hydrocarbon product comprising gasoline and/or distillate range hydrocarbons; said water being present in amount sufficient to maintain the nickel in ionic state, thereby maintaining selectivity of said second oligomerization catalyst to said liquid hydrocarbon product.

17. The process of claim 16 wherein said zeolites comprise ZSM-5.

18. The process of claim 16 wherein the feedstock consists essentially of $C_2$–$C_6$ olefins and hydrogen, wherein the second oligomerization catalyst consists essentially of Ni-exchanged acid ZSM-5, and wherein the quench water is injected between said primary stage reaction zone and said secondary stage reaction zone at a rate of at least 0.1 moles of water per mole of hydrogen.

19. The process of claim 16 wherein said quench water is injected between said primary stage reaction zone and said secondary stage reaction zone at a rate of about 0.3 to 2 moles of water per mole of hydrogen.

* * * * *